(12) United States Patent
Li

(10) Patent No.: US 7,349,098 B2
(45) Date of Patent: Mar. 25, 2008

(54) SIMULTANEOUS BEAM-FOCUS AND COHERENCE-GATE TRACKING FOR REAL-TIME OPTICAL COHERENCE TOMOGRAPHY

(75) Inventor: Xingde Li, Seattle, WA (US)

(73) Assignee: University of Washington, Seattle, WA (US)

( * ) Notice: Subject to any disclaimer, the term of this patent is extended or adjusted under 35 U.S.C. 154(b) by 122 days.

(21) Appl. No.: 11/332,780

(22) Filed: Jan. 13, 2006

(65) Prior Publication Data

US 2006/0170930 A1    Aug. 3, 2006

Related U.S. Application Data

(63) Continuation-in-part of application No. 10/880,008, filed on Jun. 28, 2004, which is a continuation-in-part of application No. 09/850,594, filed on May 7, 2001, now Pat. No. 6,975,898.

(60) Provisional application No. 60/644,335, filed on Jan. 14, 2005.

(51) Int. Cl.
*G01B 9/02* (2006.01)

(52) U.S. Cl. .................................. 356/479

(58) Field of Classification Search ................ 356/477, 356/479, 485, 486, 497; 250/227.19, 227.27
See application file for complete search history.

(56) References Cited

U.S. PATENT DOCUMENTS 4,410,235 A    10/1983    Klement et al. ......... 350/96.18

| 4,768,513 A | 9/1988 | Suzuki |
| 5,074,642 A | 12/1991 | Hicks .......................... 385/116 |

(Continued)

FOREIGN PATENT DOCUMENTS

EP    1142529 A1    10/2001

(Continued)

OTHER PUBLICATIONS

Bing Qi et al. "Dynamic Focus Control in High-Speed Optical Coherence Tomography Based on a Microelectromechanical Mirror." Optics Communications 232 (2004) 123-128. <www.elsevier.com/locate/optcom>.

(Continued)

*Primary Examiner*—Michael A. Lyons
(74) *Attorney, Agent, or Firm*—Ronald M. Anderson

(57) ABSTRACT

Method and apparatus for achieving dynamic focus tracking during real-time optical coherence tomography (OCT) by simultaneously implementing geometric focus tracking (GFT) and coherence gate tracking (CGT). GFT tracking involves changing a position of the focal point of the OCT probe in the sample during scanning. Preferably, the focal point is moved relative to the sample without disrupting the Gaussian beam profile of the scanner. CGT involves determining a change in the optical path length of the sample arm due to the GFT, and calculating the change in the optical path length in the reference arm required to maintain an equivalent optical path length in both the sample arm and the reference arm. The reference arm is then translated by the required amount, to maximize the OCT signal. A lateral priority scanning technique is employed, and this technique can be implemented using a single optical fiber suitable for endoscopic use.

20 Claims, 7 Drawing Sheets

U.S. PATENT DOCUMENTS

| | | | |
|---|---|---|---|
| 5,172,685 | A | 12/1992 | Nudelman |
| 5,247,174 | A | 9/1993 | Berman ................... 250/235 |
| 5,272,330 | A | 12/1993 | Betzig et al. ............. 250/216 |
| 5,394,500 | A | 2/1995 | Marchman ................ 385/123 |
| 5,425,123 | A | 6/1995 | Hicks ....................... 385/117 |
| 5,480,046 | A | 1/1996 | Filas et al. ...................... 216/7 |
| 5,570,441 | A | 10/1996 | Filas et al. .................. 385/43 |
| 5,703,979 | A | 12/1997 | Filas et al. .................. 385/43 |
| 5,715,337 | A | 2/1998 | Spitzer et al. ................ 385/4 |
| 5,727,098 | A | 3/1998 | Jacobson ..................... 385/31 |
| 6,046,720 | A | 4/2000 | Melville et al. ............ 345/108 |
| 6,091,067 | A | 7/2000 | Drobot et al. .............. 250/234 |
| 6,161,035 | A | 12/2000 | Furusawa ................... 600/476 |
| 6,211,904 | B1 | 4/2001 | Adair et al. .................... 458/76 |
| 6,294,775 | B1 | 9/2001 | Seibel et al. ............. 250/208.1 |
| 6,327,493 | B1 | 12/2001 | Ozawa et al. ............... 600/476 |
| 6,485,413 | B1 | 11/2002 | Boppart et al. ............. 600/160 |
| 7,023,558 | B2 * | 4/2006 | Fee et al. ................... 356/479 |
| 2001/0055462 | A1 | 12/2001 | Seibel ........................ 385/147 |
| 2002/0064341 | A1 | 5/2002 | Fauver et al. ................. 385/25 |
| 2004/0181148 | A1 * | 9/2004 | Uchiyama et al. .......... 600/425 |

FOREIGN PATENT DOCUMENTS

JP    2001174744 A2    6/2001

OTHER PUBLICATIONS

D. Huang, E.A. Swanson, C.P. Lin, J.S. Schuman, W.G. Stinson, W. Chang, M.R. Hee, T. Flotte, K. Gregory, C.A. Puliafito, and J.G. Fujimoto. "Optical Coherence Tomography." Science, 254, 1178-1181 (1991).

W. Drexler, U. Morgner, F.X. Kartner, C. Pitris, S.A. Boppart, X.D. Li, E.P. Ippen, and J.G. Fujimoto. "In vivo ultrahigh-resolution optical coherence tomography." Optics Letters, 24, 1221-1223 (1999).

M. Ohmi, T. Kurata, M. Sekimoto, and M. Haruna. "Quasi in-focus optical coherence tomography." Japanese Journal of Applied Physics Part 1-Regular Papers Short Notes & Review Papers, 43, 845-849 (2004).

Z.P. Chen, T.E. Milner, D. Dave, and J.S. Nelson, "Optical Doppler tomographic imaging of fluid flow velocity in highly scattering media." Optics Letters, 22, 64-66 (1997).

J.M. Schmitt, S.L. Lee, and K.M. Yung. "An optical coherence microscope with enhanced resolving power in thick tissue." Optics Communications, 142, 203-207 (1997).

F. Lexer, C.K. Hitzenberger, W. Drexler, S. Molebny, H. Sattmann, M. Sticker, and A.F. Fercher. "Dynamic coherent focus OCT with depth-independent transversal resolution." Journal of Modern Optics, 46, 541-553 (1999).

B. Qi, A.P. Himmer, L.M. Gordon, X.D.V. Yang, L.D. Dickensheets, and I.A. Vitkin. "Dynamic focus control in high-speed optical coherence tomography based on a microelectromechanical mirror." Optics Communications, 232, 123-128 (2004).

V.X.D. Yang, N. Munce, J. Pekar, M.L. Gordon, S. Lo, N.E. Marcon, B.C. Wilson, and I.A. Vitkin, "Micromachined array tip for multifocus fiber-based optical coherence tomography." Optics Letters, 29, 1754-1756 (2004).

X.M. Liu, M.J. Cobb, Y.C. Chen, M.B. Kimmey, and X.D. Li. "Rapid-scanning forward-imaging miniature endoscope for real-time optical coherence tomography." Optics Letters, 29, 1763-1765 (2004).

A.G. Podoleanu, J.A. Rogers, and D.A. Jackson. "Three dimensional OCT images from retina and skin." Optics Express, 7, 292-298 (2000).

Y.C. Chen and X.D. Li. "Dispersion management up to the third order for real-time optical coherence tomography involving a phase or frequency modulator." Optics Express, 12, 5968-5978 (2004).

G.J. Tearney, M.E. Brezinski, J.F. Southern, B.E. Bouma, M.R. Hee, and J.G. Fujimoto. "Determination of the Refractive-Index of Highly Scattering Human Tissue by Optical Coherence Tomography." Optics Letters, 20, 2258-2260 (1995).

* cited by examiner

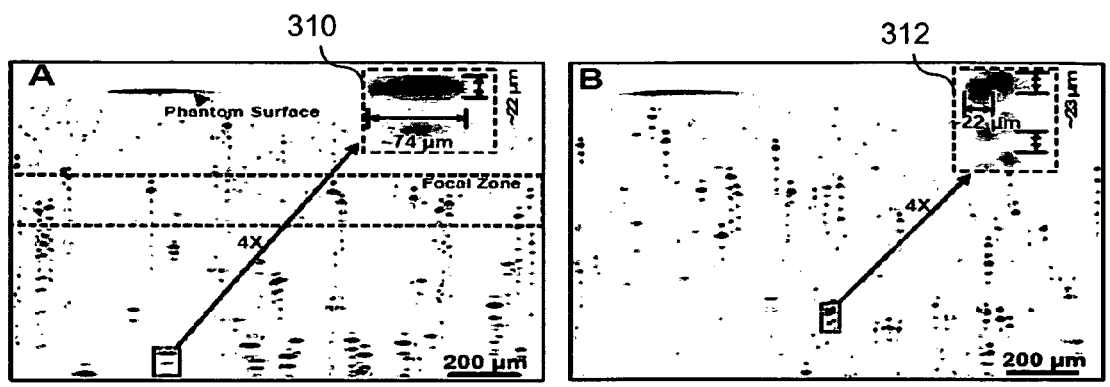
*FIG. 16A*  *FIG. 16B*
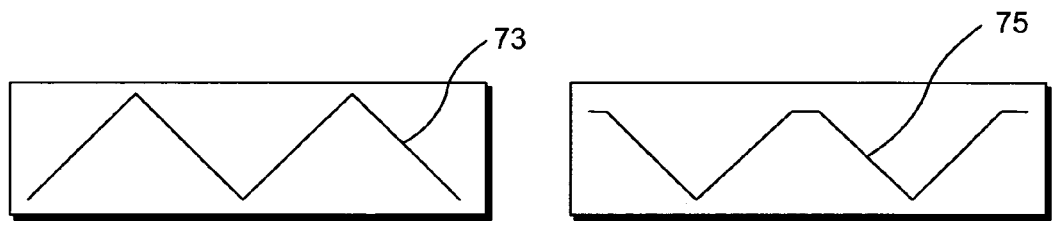
*FIG. 16C*  *FIG. 16D*
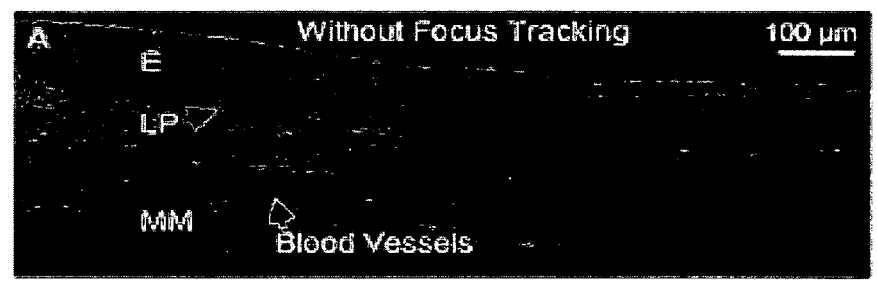
*FIG. 17A*
*FIG. 17B*

SIMULTANEOUS BEAM-FOCUS AND COHERENCE-GATE TRACKING FOR REAL-TIME OPTICAL COHERENCE TOMOGRAPHY

RELATED APPLICATIONS

This application is based on a prior provisional application, Ser. No. 60/644,335, filed on Jan. 14, 2005, the benefit of the filing date of which is hereby claimed under 35 U.S.C. § 119(e). This application is further a continuation-in-part application of a prior U.S. patent application Ser. No. 10/880,008, filed on Jun. 28, 2004, which itself is a continuation-in-part of a U.S. patent application Ser. No. 09/850,594, filed on May 7, 2001 now U.S. Pat. No. 6,975,898, the benefit of the filing dates of which is hereby claimed under 35 U.S.C. § 120.

GOVERNMENT RIGHTS

This invention was funded at least in part with a grant (No. 1 R21 CA96633-0) from the National Institutes of Health and a grant (No. BES-0348720) from the National Science Foundation, and the U.S. government may have certain rights in this invention.

BACKGROUND

Optical Coherence Tomography (OCT) is an emerging non-invasive biomedical imaging technology that can perform cross-sectional imaging of tissue microstructures in vivo and in real-time. OCT is analogous to ultrasound, except that it uses low coherence light, rather than acoustic waves. The echo delay time or the depth of light backscattered from the tissue is measured using a technique referred to as low coherence interferometry.

OCT has significant advantages over other medical imaging technologies. Medical ultrasound, magnetic resonance imaging (MRI), and confocal microscopy are ill suited to morphological tissue imaging, as ultrasound and MRI have insufficient resolution for imaging microstructures, while confocal microscopy lacks the ability to image deeply enough (i.e., beyond several hundred micrometers in highly scattering tissues), which is required for morphological tissue imaging.

As indicated above, a fundamental aspect of OCT is the use of low coherence interferometry. In conventional laser interferometry, the interference of light occurs over a distance of meters. In OCT, the use of broadband light sources (i.e., light sources that can emit light over a broad range of frequencies) enables the interference to be generated within a distance of micrometers. Such broadband light sources include super luminescent diodes (i.e., super bright light emitting diodes (LEDs)) and extremely short pulsed lasers (i.e., femto second lasers). White light can also be used as a broadband source.

Essentially, the combination of backscattered light from the sample arm and reference light from the reference arm gives rise to an interference pattern, but only if light from both arms have traveled "substantially the same" optical distance (where "substantially the same" indicates a difference of less than a coherence length). By scanning the mirror in the reference arm, a reflectivity profile of the sample can be obtained. Areas of the sample that reflect back larger amounts of light will create greater interference than areas that reflect back smaller amounts of light. Any light that is outside the short coherence length will not generate any interference. This reflectivity profile, referred to as an A-scan, contains information about the spatial dimensions and location of structures within the sample. An OCT image (i.e., a cross-sectional tomograph generally referred to as a B-scan), may be achieved by laterally combining multiple adjacent axial scans at different transverse positions by utilizing a depth-priority imaging sequence (e.g., fast axial scanning followed by slow transverse scanning).

FIG. 1 (Prior Art) schematically illustrates a conventional OCT system. This system includes a Michelson interferometer that uses a low coherence light source 20. The light source is coupled to an OCT probe 24 in the sample arm and to a reference arm 28 through an optic fiber coupler or beam splitter 22. The sample arm delivers an optical beam from the light source to a target 26 (generally a tissue sample) and collects the backscattered light. The reference arm performs depth scanning by using a translating retro-reflective mirror or a phase-controlled scanning delay line (not separately shown). A backscattered intensity versus depth data set is developed with an axial scan. Two- or three-dimensional data sets formed by multiple adjacent axial scans are obtained by scanning the OCT beam along the transverse direction after each axial scan. A photodetector 30 produces a corresponding analog signal comprising the data set. The analog signal is processed by detection electronics module 32, which produces corresponding digital data. The resulting data set can be displayed using a computer 38, as a false-color or gray-scale map, to form a cross-sectional OCT image.

Unlike confocal microscopy, the transverse and axial resolutions of OCT are determined independently. The axial resolution $\Delta z$ is based on the coherence length of the light source and is inversely proportional to the source spectrum bandwidth $\Delta \lambda$, according to the following relationship:

$$\Delta z = \left(\frac{2\ln 2}{\pi}\right)\left(\frac{\lambda_0^2}{\Delta \lambda}\right) \quad (1)$$

where $\lambda_0$ is the source center wavelength. The transverse resolution, $\Delta x$, is determined by the transverse focused spot size, in a manner similar to that in conventional microscopy, according to the following relationship:

$$\Delta x = \frac{2\lambda}{\pi} \bigg/ \frac{d}{2f} \quad (2)$$

where d is the beam spot size on the objective lens, and f is the focal length of the objective lens.

Implementing real-time OCT with continuous focus tracking in a depth-priority imaging sequence can be very challenging, since an extremely high tracking speed (on the order of a few meters/second) and a high repetition rate (in the kHz range) are required. Focus tracking is not critical when using a large transverse focused spot size. However, as a tighter focus (or higher transverse resolution) is utilized, the transverse resolution will deteriorate faster at depths farther from the focal plane. The depth of focus b (or the confocal parameter) reduces quadratically with the spot size diameter $\Delta x$ according to the following relationship:

$$b = \frac{\pi \Delta x^2}{2\lambda} \quad (3)$$

For example, the depth of focus reduces from about 200 μm to about 50 μm when the transverse resolution increases from 10 to 5 μm. Conventional OCT has a relatively low transverse resolution, between about 20 μm and about 40 μm, and focus tracking is not generally necessary for low resolution OCT. However, low transverse resolution degrades image contrast. Even with coherence gating along the axial direction, photons that are backscattered within the focal spot size by different scatterers (e.g., by cells or cell organelles) will likely be simultaneously detected and averaged, causing loss of contrast. Therefore, a high transverse resolution is much preferred. To maintain a high transverse resolution at various depths, focus tracking is needed. As indicated in Equation (3), small changes in the spot size diameter result in large changes to the depth of focus. Thus, dynamic focus tracking becomes very important for maintaining the focused spot size throughout the entire imaging depth.

Conventional real-time OCT imaging is achieved by fast axial scanning followed by slow transverse scanning, and the image consists of multiple adjacent axial scans at different transverse locations. A 2-3 mm axial scan generally takes less than 0.5 milliseconds during real-time imaging, requiring focus tracking at a velocity of about 4-6 meters per second, which is extremely difficult to achieve in a compact scanning device. FIG. 2 illustrates the rapid depth scanning of tissue 42 by an incident beam 40, and the relatively slow transverse scans that are used. In this conventional technique for OCT scanning, focus tracking means that the focus point is rapidly tracked at each different transverse location before moving to the next transverse location, which is very challenging to achieve.

One simple non-dynamic focus tracking approach is to acquire a sequence of images with the focus gradually shifted into the sample, and then to fuse together the in-focus image zones through post-image processing. Unfortunately, precise image registration is difficult to achieve, and the effective frame rate is reduced by at least the number of focal zones taken to generate one "in-focus" image. In contrast, dynamic focus tracking seeks to simultaneously track the imaging beam focus and the coherence gate throughout the entire imaging depth, by maintaining a preferably zero or near zero optical path length (OPL) difference between the reference and sample arms, as determined from the focal plane within the imaging depth.

It would be desirable to provide alternative techniques for implementing focus tracking in OCT imaging. It would be particularly desirable to provide a technique enabling a relatively fast frame rate, and which enables the beam spot size to be maintained over a variety of focal depths. Relatively fast frame rates will facilitate the use of OCT imaging with live tissue (i.e., live biological specimens). Preferably, the frame rate will be faster than the respiratory rate of the specimen, to avoid blurring due to respiratory activity.

SUMMARY

One aspect of the concepts disclosed herein relates to a method for OCT imaging using dynamic focus tracking for improved image quality. Dynamic focus tracking is achieved by simultaneously implementing geometric focus tracking and coherence gate tracking in a synchronized fashion.

Geometric focus tracking involves changing the position of the focal point of the OCT probe in the sample during scanning. Preferably, the focal point is moved relative to the sample without disrupting the Gaussian beam profile of the OCT probe's optical system. Disrupting the Gaussian beam profile would result in changing the resolution of the optical system during scanning. The present technique improves OCT image quality by controlling the resolution during scanning. Thus, changing the Gaussian beam profile during scanning is not preferred. For samples that can be readily moved relative to the OCT probe, focus tracking can be achieved by translating the sample itself. In many implementations, particularly where the OCT probe is configured for endoscopic or internal use, it is preferable to incorporate a mechanism to translate the OCT probe's optics to achieve geometric focus tracking. A plurality of specific techniques are described in greater detail herein for achieving such a translation. In general, a translation of only a few millimeters is required. In some embodiments, a single optical fiber OCT probe includes a micromotor that can be used to translate the scanner and optics assembly. In another embodiment, an externally disposed motor is used to transfer a longitudinal motion to the distal end of the sample probe to achieve the desired translation. In yet another embodiment, an electro-active polymer is selectively energized to linearly translate the optics of the OCT probe. In still other embodiments, changes in pressure are used to achieve the geometric focus tracking.

Coherence gate tracking involves determining the change in the OPL of the sample arm due to the geometric focus tracking, and calculating the change in the OPL in the reference arm required to maintain an equivalent OPL in both the sample arm and the reference arm. The reference arm is then translated by the required amount, to maintain the same OPL in the reference arm and the sample arm. It should be understood that the same OPL length, as that phrase is used herein and in the claims that follow, is intended to indicate that an OPL length in the sample arm and an OPL in the reference arm differ by a small amount (preferably within the coherence length). The corresponding movement of the optics in the reference arm is required to maximize the OCT signal (by keeping the OPLs in the two arms equal or nearly equal). As those of ordinary skill in the art will recognize, the change in the OPL in the sample arm does not simply correspond to a linear translation of the OCT probe. Determining the change in the OPL in the sample arm due to the geometric focus tracking requires taking into account the linear translation distance in the sample arm, the index of refraction of the medium above the sample, the index of refraction of the sample, and the numerical aperture of the objective, enabling the total OPL change to be calculated. Once the OPL change is determined, similar calculations are used to determine by how much the optics in the reference arm should be translated to achieve a substantially equal change, in order to keep the coherence gate collocated with the geometric beam focus, and to synchronize the OPL change in the sample arm during focus tracking.

Another concept disclosed herein is an OCT imaging system that has been configured to simultaneously implement geometric focus tracking and coherence gate tracking. Such a system will incorporate an OCT imaging probe configured to facilitate geometric focus tracking, preferably without changing the Gaussian beam profile of the optics. The system will also incorporate a processor configured to determine the change in the OPL in the sample arm due to the geometric focus tracking, to calculate a corresponding change required in the OPL of the reference arm, to ensure that the OPLs in the reference arm and sample arm are equal, and to control a mechanism to translate the reference arm to achieve OPL synchronization. A translation stage can be used as the mechanism.

Significantly, the concepts disclosed herein involve a modification of the conventional OCT imaging sequence. As noted above with respect to FIG. 2, conventional real-time OCT imaging is achieved by fast axial scanning followed by slow transverse scanning, and the OCT image includes multiple adjacent axial scans at different transverse locations. In the context of the dynamic focus tracking technique disclosed herein, the conventional OCT image acquisition sequence is reversed, by employing fast transverse scanning followed by slow depth (or axial) scanning. The OCT image is then based on multiple transverse scans at different depths, as is schematically illustrated in FIG. 3. This scanning paradigm is referred to herein and the claims that follow as lateral priority scanning. Significantly, in lateral priority scanning, the depth scanning speed is reduced by a factor of $N_{xpixel}$ (the number of transverse pixels, often in the range of 500-1,000). Thus, in the lateral priority scanning scheme, fast depth scanning is not required, making real-time focus tracking achievable. The reduced depth scanning speed also permits using a translating retro-reflective mirror in the OCT reference arm to perform OPL (or depth) scanning. In a particularly preferred implementation, lateral priority scanning is achieved by using a rapid scanning single-mode fiber, whose fast scanning tip is imaged onto the sample (or tissue).

In this new approach to achieve real-time OCT imaging with dynamic focus tracking, the rapid scanning fiber (suitable for incorporation into an endoscope) is mechanically translated at up to about a few tens of frames per second, using a lateral priority imaging sequence. The reference arm length is scanned synchronously to track the coherence gate with the beam focus, in order to maximize the OCT signal at the focus during focus tracking. This approach enables a compact OCT instrument (i.e., an endoscopic-sized instrument) incorporating dynamic focus tracking to be achieved, with a frame rate faster than most biological respiratory rates.

Significantly, the scanning fiber in the OCT probe (i.e., in the sample arm) requires a relatively small translation (about one millimeter) to enable focus tracking and lateral priority imaging to be achieved. As noted above, several techniques and structures can be used to longitudinally (preferably linearly) translate the scanning fiber.

This Summary has been provided to introduce a few concepts in a simplified form that are further described in detail below in the Description. However, this Summary is not intended to identify key or essential features of the claimed subject matter, nor is it intended to be used as an aid in determining the scope of the claimed subject matter.

DRAWINGS

Various aspects and attendant advantages of one or more exemplary embodiments and modifications thereto will become more readily appreciated as the same becomes better understood by reference to the following detailed description, when taken in conjunction with the accompanying drawings, wherein.

Figures 6A, 6B:
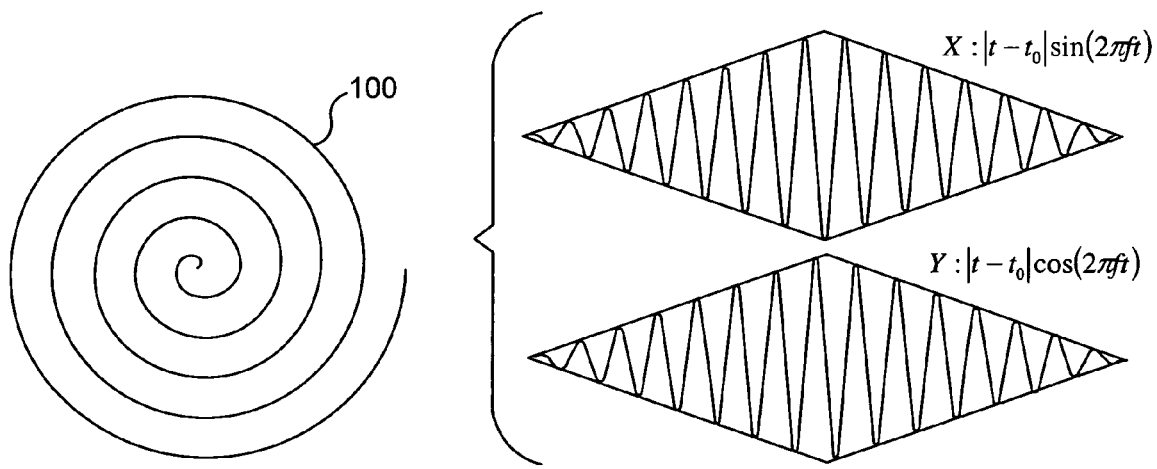
Figure 7:
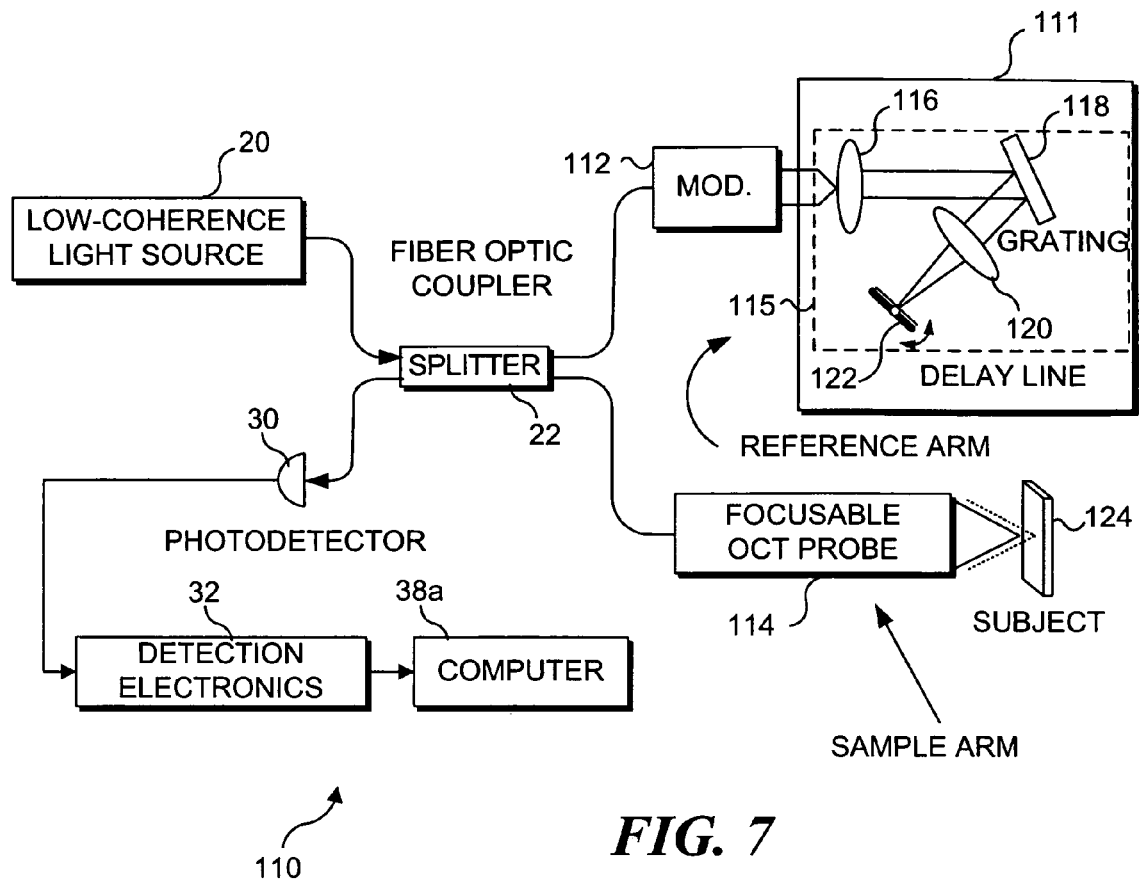
Figure 8:
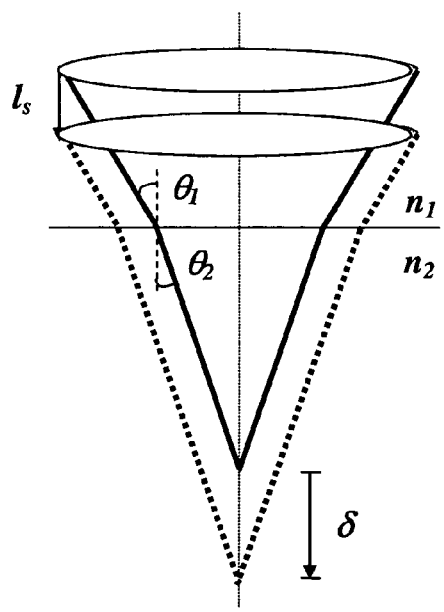
Figure 9:
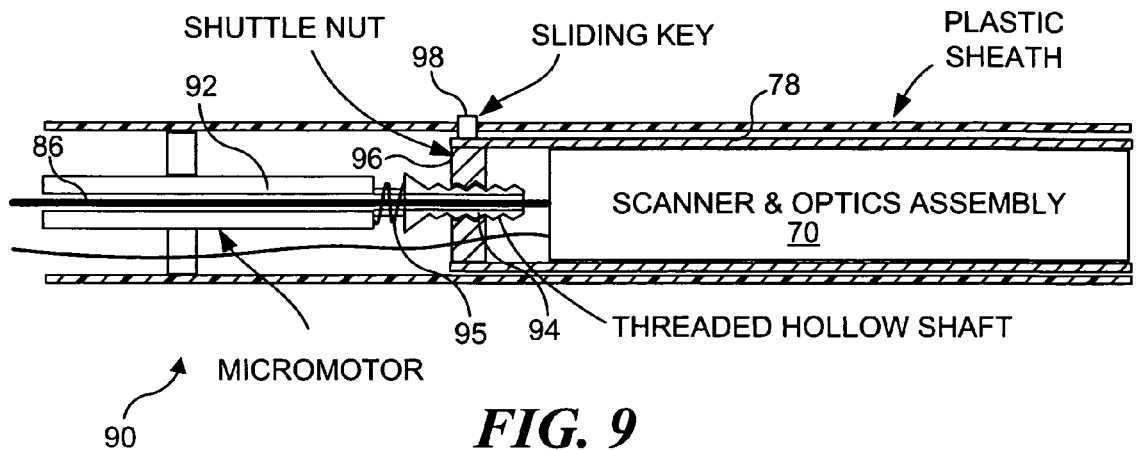
Figure 10:
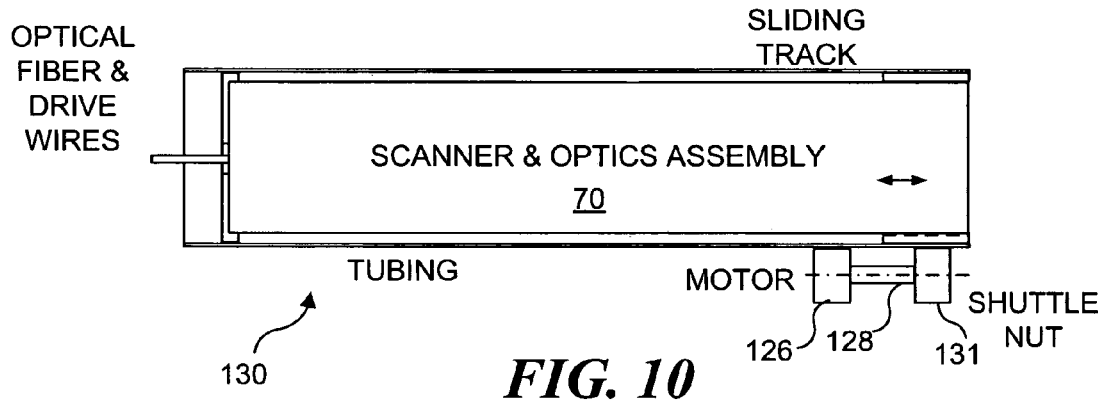
Figure 11:
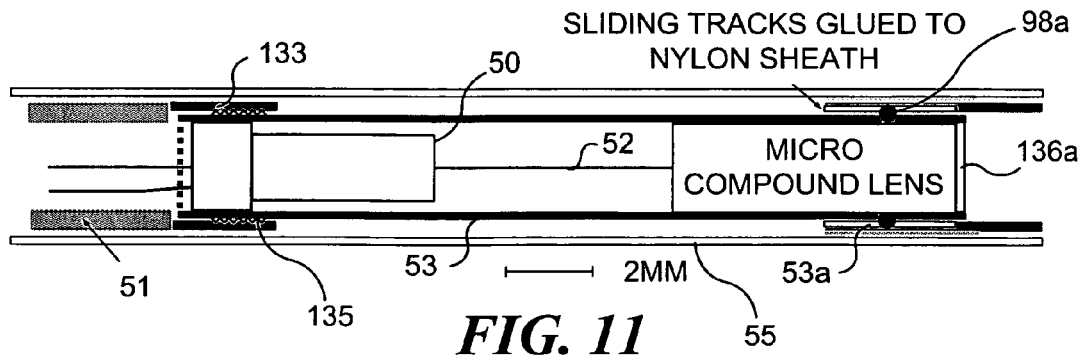
Figure 12A:
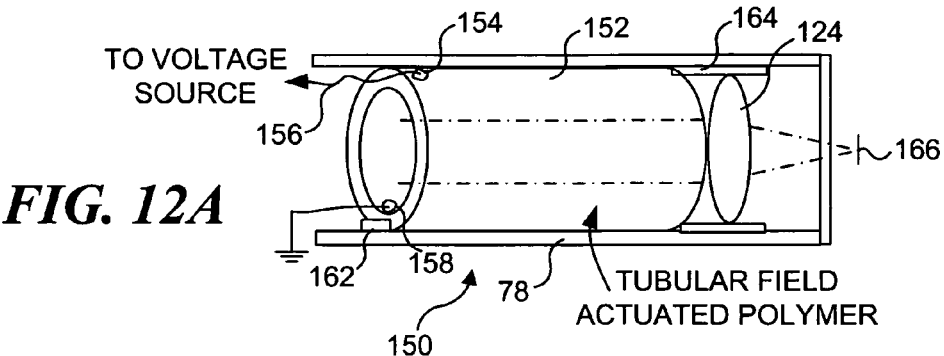
Figure 12B:
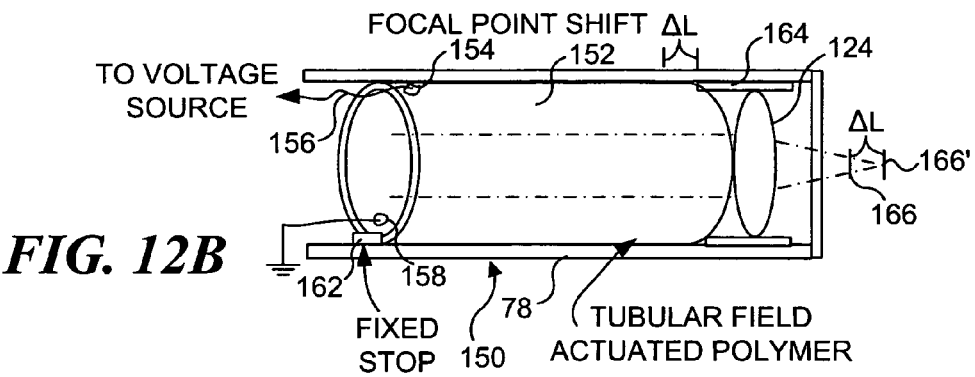
Figure 13:
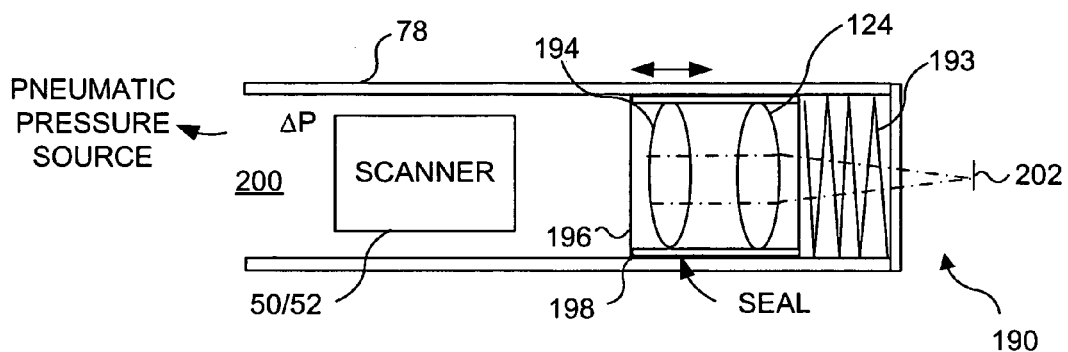
Figure 14:
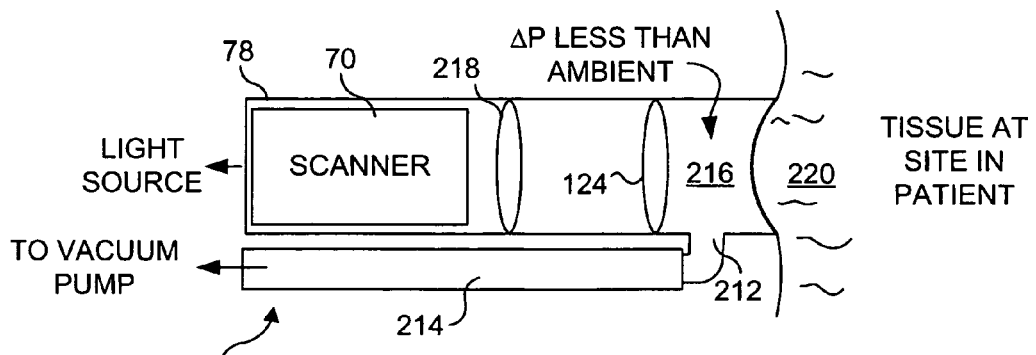
Figure 15A:
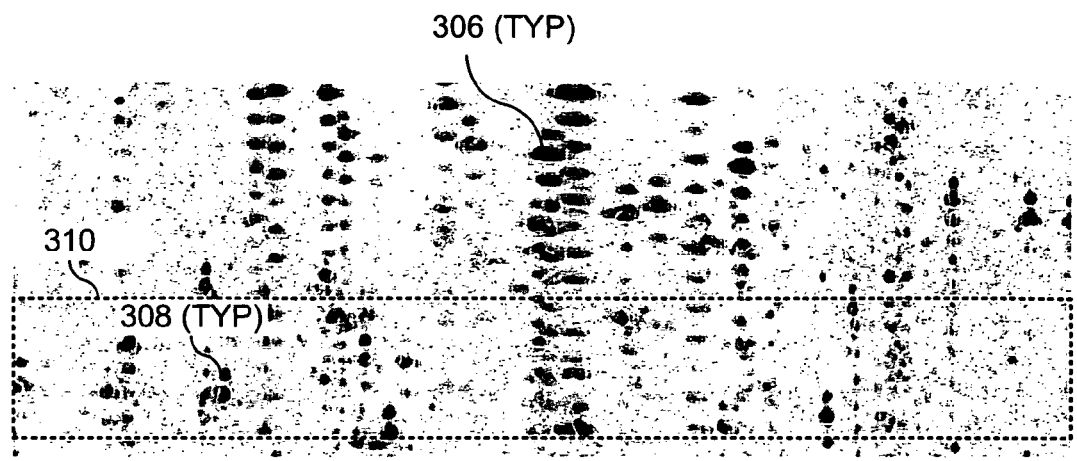
Figure 15B:
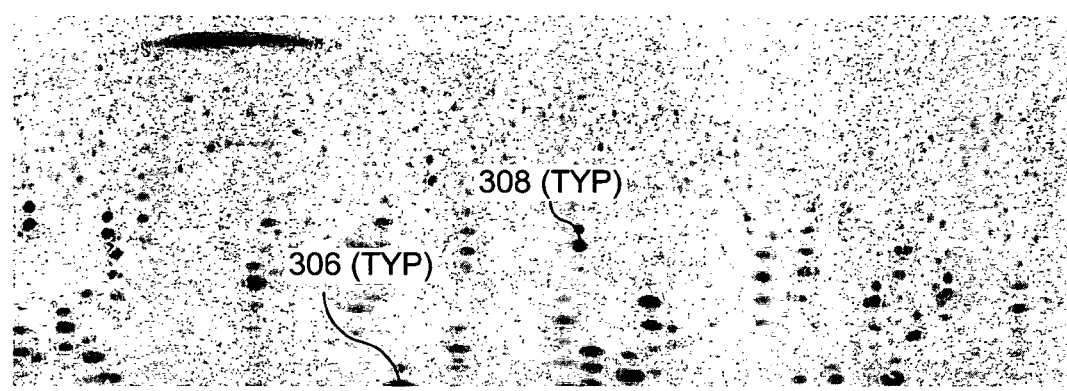
Figure 15C:
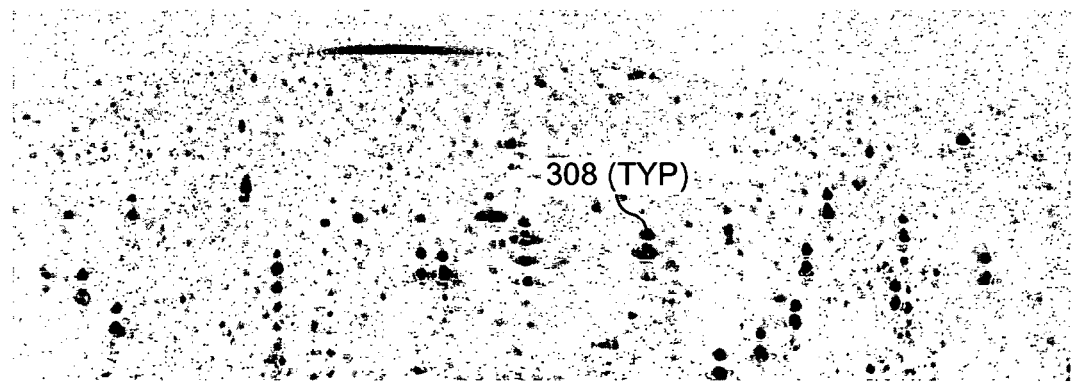

FIG. 6A schematically illustrates a spiral scan pattern that is useful in scanning at each depth, in accord with the concepts disclosed herein;

FIG. 6B illustrates triangularly modulated sine and cosine signals that drive a cantilevered optical fiber to vibrate relative to X and Y orthogonal axes in the exemplary optical fiber scanners disclosed herein;

FIG. 7 is a schematic block diagram of an OCT system configured to implement simultaneous geometric focus tracking and coherence gate tracking, in accord with the concepts disclosed herein;

FIG. 8 schematically illustrates a linear translation of optics in a scanner as described herein, in order to achieve geometric focus tracking while maintaining focal size, showing the geometry for calculating the change of the OPL in the sample arm during geometric beam focus tracking;

FIG. 9 is a schematic cut-away side elevational view of an embodiment of a longitudinal drive for use in an optical fiber-based endoscopic OCT scanner for use in the OCT system of FIG. 7, to facilitate varying the depth of the transverse scan;

FIG. 10 schematically illustrates an alternative embodiment of an optical fiber-based OCT scanner for use in the OCT system of FIG. 7, which also utilizes a micromotor to facilitate varying the depth of the transverse scan, the motor being disposed outside of a housing at a distal end of an OCT probe;

FIG. 11 schematically illustrates an optical fiber-based OCT scanner for use in the OCT system of FIG. 7, which utilizes a micromotor to facilitate varying the depth of the transverse scan, the motor being disposed at a proximal end of an endoscopic OCT probe;

FIGS. 12A and 12B schematically illustrate a portion of an optical fiber-based OCT scanner for use in the OCT system of FIG. 7, which uses a tubular field-actuated polymer driver to vary the scanning depth (i.e., the depth of the focal point of the optical fiber scanner);

FIG. 13 is a schematic cut-away view of an optical fiber-based OCT scanner for use in the OCT system of FIG. 7, showing how a varying pneumatic pressure is applied to a lens carrier, producing a force that varies the location of the focal point of a lens, to enable transverse scanning at different depths;

FIG. 14 is a schematic cut-away view of yet another optical fiber-based OCT scanner for use in the OCT system of FIG. 7, in which a vacuum source is applied to vary the longitudinal position of tissue drawn into an open distal end of the optical fiber scanner, to vary the longitudinal location of the focal point for scanning at different depths in the tissue;

FIG. 15A is an OCT image of a gelatin phantom embedded with 25 μm-diameter polystyrene microspheres, acquired without employing geometric focus tracking or coherence gate tracking;

FIG. 15B is an OCT image of a gelatin phantom embedded with 25 μm-diameter polystyrene microspheres, acquired by employing geometric focus tracking but not coherence gate tracking;

FIG. 15C is an OCT image of a gelatin phantom embedded with 25 μm-diameter polystyrene microspheres, acquired by employing simultaneous geometric focus tracking and coherence gate tracking;

FIG. 16A is an OCT image of a gelatin phantom embedded with 25 μm-diameter polystyrene microspheres, acquired without employing geometric focus tracking or coherence gate tracking;

FIG. 16B is an OCT image of a gelatin phantom embedded with 25 μm-diameter polystyrene microspheres, acquired by employing simultaneous geometric focus tracking and coherence gate tracking;

FIG. 16C is a waveform used in connection with the acquisition of the OCT image of FIG. 16A;

FIG. 16D is a waveform used in connection with the acquisition of the OCT image of FIG. 16B;

FIG. 17A is an OCT image of a rabbit esophagus obtained without using dynamic real-time focus tracking based on simultaneous geometric focus tracking and coherence gate tracking; and FIG. 17B is an OCT image of a rabbit esophagus obtained using dynamic real-time focus tracking based on simultaneous geometric focus tracking and coherence gate tracking, showing that the techniques disclosed herein provide an OCT image with enhanced contrast.

DESCRIPTION

Figures and Disclosed Embodiments Are Not Limiting

Exemplary embodiments are illustrated in referenced Figures of the drawings. It is intended that the embodiments and Figures disclosed herein are to be considered illustrative rather than restrictive.

Figure 4:
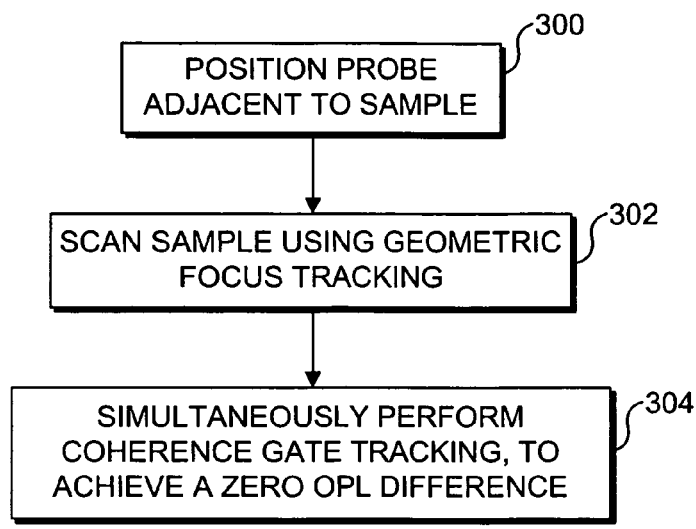
FIG. 4 is a flowchart illustrating exemplary steps for performing the technique disclosed herein.

FIG. 4 is high-level flowchart illustrating exemplary steps for carrying out the technique disclosed herein. In a block 300, an OCT probe is positioned adjacent to a sample. In a block 302, geometric focus tracking is implemented during lateral priority scanning. As noted above, geometric focus tracking involves changing the position of the focal point of the OCT probe in the sample during scanning, which changes the OPL in the sample arm. In a block 304, coherence gate tracking is simultaneously implemented. As noted above, coherence gate tracking involves determining the change in the OPL of the sample arm due to the geometric focus tracking, and calculating the change in the OPL in the reference arm that is required to maintain an equal OPL in both the sample arm and the reference arm. The reference arm is then translated by the required amount, to maintain the same OPL in the reference arm and the sample arm. Note that the smaller the difference between the OPL in the sample arm and the OPL in the reference arm is, the higher will be the quality of the OTC signal that is produced. While the current technique does not guarantee that there will be no OPL difference, this technique represents a significant improvement as compared to conventional OCT imaging, which does not provide focus tracking or simultaneous tracking of the geometric beam focus and the coherence gate. Details of this technique are described below.

Figure 2:
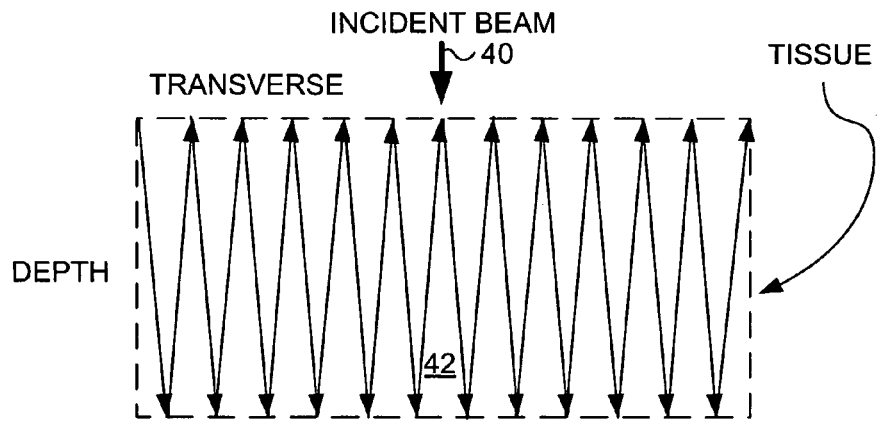
FIG. 2 (Prior Art) is a schematic representation of the scanning pattern of a conventional OCT system, which rapidly scans at different depths, moves transversely to a different point, and then again rapidly scans at different depths, with the result that real-time focus tracking is difficult.
Figure 3:
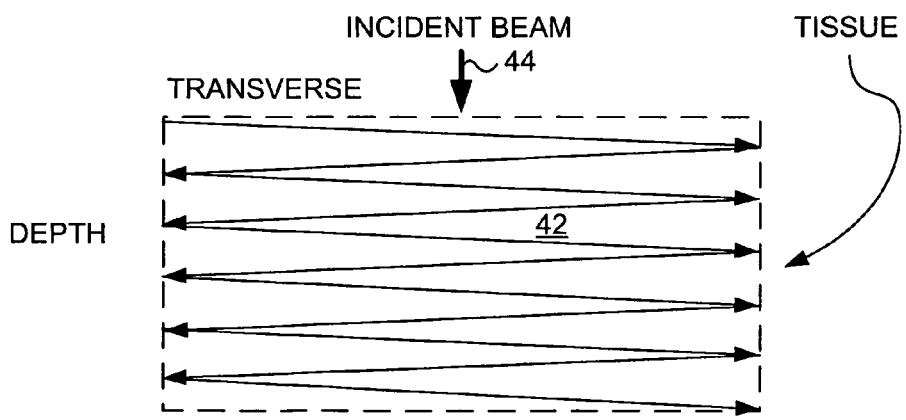
FIG. 3 is a schematic representation of a scanning pattern used in connection with the concepts disclosed herein, which provide for rapidly scanning transversely at a given depth, while slowly moving to a different depth, and again rapidly scanning transversely, thereby facilitating focus tracking.

A key advantage of the approach that is described herein over other prior art OCT scanning systems is that the depth focus tracking is varied relatively slowly compared to the transverse scanning speed (i.e., lateral priority scanning is employed). Unlike prior art OCT scanning systems that employ the scanning procedure illustrated in FIG. 2, the present technique scans transversely relatively rapidly at a current depth, moves the focus point to a different depth, and then repeats the rapid transverse scan at the new depth. FIG. 3 illustrates this scanning procedure in tissue 42 for an incident beam 44 that scans transversely at a current depth, before shifting to a new and different depth. Accordingly, because the movement of the focal point through different depths is performed more slowly than in prior art OCT systems, it is possible to track the focus point in depth for each different transverse position (i.e., to achieve dynamic focus tracking). In contrast to prior OCT scanning techniques (i.e., the scanning technique of FIG. 2), the transverse scanning/lateral priority scanning in the present technique is performed much more rapidly, compared to the rate at which the focus point is shifted, and it completes a transverse scan at each of successively different depths or within the thickness of the slice, before shifting to the next depth. An exemplary optical fiber-based OCT imaging probe, described in greater detail below, is ideally suited for this scanning technique, since it includes a cantilevered optical fiber that is readily driven to scan along a linear path, or two-dimensionally in a desired pattern, such as in a spiral, propeller, Lissajous, or any other two-dimensional scanning pattern.

Figure 5:
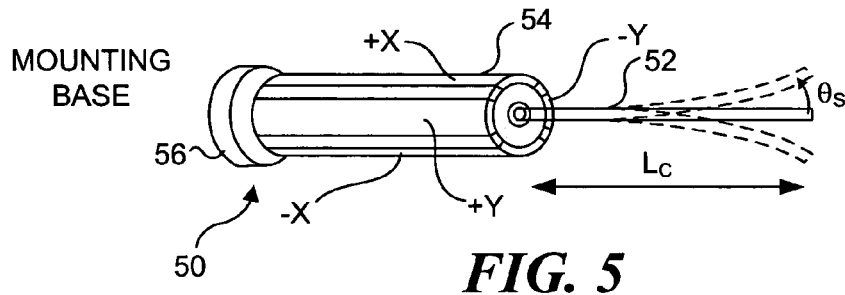
FIG. 5 is a schematic isometric view of an optical fiber scanner for use in the present approach.

An optical fiber scanner 50 that is suitable for use in the dynamic focus tracking disclosed herein is illustrated in FIG. 5. Optical fiber scanner 50 includes a cantilevered optical fiber 52 (which is preferably single mode) that is driven in either one or two (e.g., orthogonal) directions by a tubular lead zirconate titanate (PZT) actuator 54 (or using any other suitable piezoelectric or electromagnetic actuator). The PZT actuator is supported by a base 56. Although not shown in this simplified drawing, a gradient index (GRIN) lens or other type of rod lens may be fused to the distal end of the cantilevered optical fiber, for focusing light passing through the optical fiber. Pairs of electrodes (one electrode for each of the X and −X, and Y and −Y axes, each electrode being disposed on a different quadrant) are included on the PZT actuator for coupling to a suitable drive signal. When these electrodes are energized with appropriate drive signal(s), the PZT actuator causes cantilevered optical fiber 52 to vibrate and thus scan in a desired pattern. For example, when sine and cosine waves having the waveforms shown in FIG. 6B are respectively applied to the two pairs of electrodes, the resulting scan will be a spiral, as shown in FIG. 6A. A circular scan is produced when the horizontal (X) and vertical (Y) resonance vibrations are at the same frequency and equal in amplitude, but 90° out of phase. The space-filling spiral scan of FIG. 6A is generated when both amplitudes are modulated in a triangle pattern, while the relative phase is kept constant. Each half cycle of the triangle modulation in FIG. 6B is a frame, and the rising half cycle of the triangular modulation generates an opening spiral pattern, while the falling half cycle generates a closing spiral pattern. For imaging at a constant sampling rate, the central portion of the spiral scan field is over sampled, and the periphery is under sampled. Interpolation along the annulus can be performed to fill in the pixels that are not sampled, and decimation can be applied to the over sampled pixels. Spiral scanning has the advantage of using only a single tubular PZT to generate the 2-D spiral scans from within a small cylindrical enclosure.

In an initial prototype, a 7.2 mm-long PZT actuator 54 having a 1.5 mm diameter was used. The proximal end of the PZT tube was adhesively attached to base 56, which had a slightly larger diameter (i.e., 1.8 mm) than the PZT actuator. A thin holder (not separately shown) was attached within the distal end of the PZT actuator to support the cantilevered optical fiber during its vibration (i.e., while pivoting with respect to the center of the holder). The distal tip of the cantilevered optical fiber was cleaved at an 8° angled bevel to reduce the back reflection of light at its junction with the GRIN lens. The measured resonant frequency of single mode cantilevered optical fiber 52, which was about 8.5 mm long, was about 1.4 kHz. A GRIN lens (not separately identified) having a 0.25-pitch length (numerical aperture (NA)=0.46), and a 1.8-mm diameter was added to the prototype. The cantilevered optical fiber and GRIN lens were encased within a separate cap (not shown) made of a 13-gauge stainless steel hypodermic tube, which snugly slid over base 56. The proximal end of the GRIN lens (i.e., the end facing the distal tip of the cantilevered optical fiber) was polished at an 8° angled bevel to match the cleaved 8° angled bevel on the distal tip of the cantilevered optical fiber. The working-distance and the focused spot size are adjustable in this prototype by changing the object distance between the tip of cantilevered optical fiber 52 and the GRIN lens. In the prototype, a 1.5 mm object distance and a 3.5 mm working distance were chosen. The measured transverse resolution was 16 μm, with a confocal parameter of 0.32 mm. The lateral scanning range of the imaging beam on the focal plane is equal to the scanning range of the distal tip of the cantilevered optical fiber multiplied by the magnification of the GRIN lens, which is proportional to the amplitude of the applied sinusoidal PZT drive signals. For instance, a 2.5 mm lateral scanning range can be readily achieved when both pairs of electrodes are actuated with a PZT drive voltage of ±30 volts (60 volts peak-to-peak). The drive current is very small (<100 μA) due to the high capacitive impedance of the PZT electrodes. The entire endoscope was encased within a TEFLON™ plastic tube (not shown), providing extra insulation and protection. The overall diameter of the resulting scanning endoscope, including the hypodermic tube, was 2.4 mm, and the length of the rigid portion was 32 mm.

An important feature of the concepts disclosed herein is the relatively slow change in the position of the focal point, in regard to depth in a subject tissue after each transverse scan has been completed, or continuously during the transverse scanning/lateral priority scanning. This relatively slow change in the depth of the focal point in the tissue enables dynamic focus tracking to be achieved. To enable such focus tracking to be achieved, a mechanism must be provided to enable the focal point of the optical fiber to be moved. While the sample itself could be moved, for in vivo applications, it is preferable for the movement of the focal point to be achieved by the OCT probe itself. FIG. 7 schematically illustrates an exemplary OCT system 110 that is suitable for implementing this concept.

Referring to FIG. 7, OCT system 110 includes a low-coherence light source 20, preferably implemented with a super luminescent laser diode (SLD). Other advanced low-coherence light sources, such as a short-pulse laser (i.e., a femto-second pulse laser) and continuum generation in a photonic optical fiber can be used for achieving ultrahigh resolution. For the image acquisition sequence of FIG. 3, a phase or frequency modulator 112 was used in the reference arm to elevate the Doppler frequency to achieve sensitive heterodyne OCT detection (for example, the Doppler frequency can be elevated to about 1.5 MHz). Preferably, dispersion from the phase modulator crystal (not separately shown) was compensated to a third order by using a grating-based, phase-controlled optical delay line 115 that included a lens 116, a grating 118, a lens 120, and a tilting mirror 122. The slow depth scanning was performed in the phase-controlled optical delay line, and the Doppler frequency shift resulting from the delay line was set to zero by centering the beam at the rotational axis of the tilting mirror. The modulator can be implemented with an electro-optic phase modulator or an acousto-optic frequency modulator.

Significantly, OCT system 110 includes a focusable OCT probe 114 (i.e., a probe configured to enable the focal point to be translated to a different sample depth during scanning), and a computer 38a configured to control the system to achieve coherence gate tracking. Thus, OCT system 110 is designed to simultaneously achieve geometric focusing and coherence gate tracking, thereby implementing dynamic focus tracking and improving the contrast of the OCT images.

Furthermore, as described in greater detail below, OCT system 110 includes a mechanism 111 for translating the reference arm, such that the OPL of the reference arm can be synchronized to the OPL in the sample arm, to achieve coherence gate tracking. Those of ordinary skill in the art will readily recognize that many different types of translation stages are available, which are suitable for implementing mechanism 111. Significantly, the rate of translation for the reference arm is modest, on the order of several millimeters per second.

While not specifically shown in the Figure, it should be recognized that mechanism 111 is logically coupled to computer 38a, to enable computer 38a to control mechanism 111 to achieve the translation required for coherence gate tracking. Further, computer 38a will be logically coupled to modulator 112 and the reference arm optical system, to control those elements during OCT imaging. Similarly, computer 38a will be logically coupled to OCT probe 114, in order to control the scanning to achieve the desired lateral priority scanning and geometric focus tracking (although it should be recognized that one or more additional computers/processors or other types of controllers could be used to control these elements).

Need for Coherence Gate-Tracking

Linear translation of optical components in focusable OCT probe 114 is a preferred mechanism to move the focal point of the OCT scanner relative to a depth of the sample. It should be recognized that the OPL changes when the geometric focus is tracked along the scanning depth. Since the maximal OCT signal occurs when the OPLs in the reference and sample arms are equal, the coherence gate should be tracked simultaneously with the geometric beam focus during focus tracking, in order to achieve the optimal OCT signal.

To achieve coherence gate tracking, the change of the OPL in the sample arm (the change that results from the geometric focus tracking, i.e., the linear translation of the OCT probe's optical components) must first be determined. As shown in FIG. 8, when the objective lens in the sample arm moves towards the sample by a distance $l_s$ in air, the beam focus in the sample changes by a distance $\delta$. Significantly, the simultaneous geometric focusing and coherence gate tracking disclosed herein is based on changing the position of the focal point without changing the size of the focal point (i.e., without changing the Gaussian beam parameters, which would result in changing the resolution during scanning). By using simple geometric optics, the following relationship can be determined:

$$\delta = \frac{\tan\theta_1}{\tan\theta_2} l_s \quad (3)$$

where $\theta_1$ and $\theta_2$ are related by the Snell's Law, i.e., as follows:

$$n_1 \sin\theta_1 = n_2 \sin\theta_2 = N.A. \quad (4)$$

where $n_1$ and $n_2$ are respectively the index of refraction of the medium above the sample and the index of refraction of the sample, and N.A. is the numerical aperture of the objective. The total OPL change is then given by:

$$\Delta_{OPL} = n_2\delta - n_1 l_s = \left[n_2 \frac{\tan\theta_1}{\tan\theta_2} - n_1\right] = \left[n_2 \sqrt{\frac{n_2^2 - N.A.^2}{n_1^2 - N.A.^2}} - n_1\right] l_s \quad (5)$$

Clearly, in order to the track the coherence gate, the OPL in the reference arm needs to be changed accordingly by the amount of ΔOPL. For an objective of a small N.A., Eq. (5) can be approximated as:

$$\Delta_{OPL} \approx \frac{n_2^2 - n_1^2}{n_1} l_s \quad (6)$$

Without losing generality, it can be assumed that the medium above the sample is air, thus $n_1=1$. Consequently, the total OPL change $\Delta_{OPL}$ in the sample arm due to the geometric focus tracking can be closely approximated by:

$$\Delta_{OPL} \approx (n_2^2 - 1) l_s \quad (7)$$

The OPL value determined using Equation (7) indicates how much the reference arm OPL needs to be varied in order to keep the coherence gate collocated with the geometric beam focus. Thus, as the OPL in the sample arm is changed during geometric focus tracking (i.e., the linear translation of the optical components of focusable OCT probe 114), the reference arm OPL must also be changed synchronously. Computer 38a of OCT system 110 is programmed to control the geometric focus tracking of focusable OCT probe 114, to determine the OPL change required to synchronize the OPL in the reference and sample arms, and to adjust the reference arm OPL accordingly.

It should be recognized that focusable OCT probe 114 can be implemented using a variety of mechanisms in order to achieve the desired geometric focus tracking (the movement of the focal point to a different sample depth without changing the beam geometry of focal size, as indicated in FIG. 8). For example, the geometric focus tracking can be implemented by actuating an elastomeric polymer that changes length in response to an electric potential, driving a motor to rotate a shaft that shifts the focal point longitudinally, applying either a hydraulic or pneumatic pressure to overcome a spring tension and thereby shifts the focus, or controlling a pressure applied to vary a separation between tissue at a site and the distal portion of the optical fiber scanner. Each of these various approaches can thus shift the focal point longitudinally to enable transverse scanning at each different depth.

A first embodiment of a focusable OCT probe 114 is an OCT probe 90 schematically illustrated in FIG. 9, which includes a micromotor 92 disposed adjacent to optical fiber scanner and optics assembly 70 to precisely longitudinally translate the scanning endoscope assembly, i.e., the PZT actuator and imaging optics, relative to a subject that is being imaged. The working principle of a micromotor is well known in the art. For this exemplary embodiment, micromotor 92 has a 1.9 mm diameter and rotatably drives a threaded hollow shaft 94. The threaded hollow shaft has an inner diameter of more than 250 μm so that optical fiber 86 can easily pass through the open center bore of the hollow threaded shaft. In addition, the micromotor provides a substantial torque and runs at a controllable high scanning speed, with relatively low power consumption (<10 mW). As the micromotor rotates hollow threaded shaft 94, a shuttle nut 96, which engages the threads on the hollow threaded shaft, is prevented from rotating by a sliding key 98 that slides within a slot (not shown) in the plastic sheath. The shuttle nut is thus forced to move longitudinally as the hollow threaded shaft rotates within the shuttle nut. Shuttle nut 96 is coupled to a proximal end of metal hypodermic tube 78 and thus moves optical fiber scanner and optics assembly 70 longitudinally, as well. A helical spring 95 provides a biasing force against hollow threaded shaft 94, transferring the rotation of the micromotor to the hollow threaded shaft, as well as stabilizing the rotation.

Using a shuttle nut 96 having a pitch of 50 threads per inch, each rotation of the hollow threaded shaft translates the endoscope longitudinally by about 500 μm. In order to achieve a real-time depth focus tracking over a 1 mm range at an imaging rate of 10 frames/s, the required micromotor speed is about 1200 rpm. The required rpm for the target focus-tracking speed is thus well within the limits of the micromotor. A lower rpm is sufficient when using a coarse thread pitch (e.g., 30-40 threads/inch).

When the scanning endoscope is longitudinally translated during depth focus tracking, optical fiber 86, which is outside the PZT actuator, is slightly "pushed and pulled." However, the total translation is only about 1 mm, and based upon empirical experience, a 1 mm optical fiber longitudinal translation is easily absorbed by a slight bending of the optical fiber within plastic sheath 80, without damaging the optical fiber.

Alternative Exemplary Embodiments of OCT Probes Enabling Depth Focus Tracking

An exemplary embodiment 130 for varying depth focus tracking is shown in FIG. 10. Light emitted from cantilevered optical fiber 52 is focused by a lens system that includes a single lens or multiple lenses. FIG. 10 illustrates combined optical fiber scanner and optics assembly 70. To adjust the dept focus tracking, a motor 126 is energized, rotatably driving a threaded shaft 128. Threaded shaft 128 is threaded into a shuttle nut 131, and the shuttle nut is coupled to combined optical fiber scanner and optics assembly 70, so that when the shuttle nut moves longitudinally, combined optical fiber scanner and optics assembly 70 is also moved longitudinally, along a sliding track enclosed in an outer housing.

Yet another exemplary embodiment of an OCT probe configured to vary the depth at which the focus point is located in a subject being scanned is shown in FIG. 11. A precision direct current (DC) motor (not separately shown) is disposed at the proximal end of the endoscope. A shuttle nut 133 that matches threads 135 (preferably having about 80 turns/inch) will be screwed onto the endoscope tube. The shuttle nut is then attached to a hollow wire 51 (e.g., a speedometer cable), and the speedometer cable is rotated by the DC motor at the proximal end of the endoscope, under the control of a computer (not shown). The fiber-scanner drive-wires and the single-mode fiber will be encased within the speedometer cable. A thin, guiding tube 53 (e.g., made of metal), which has two sliding keys 98a on its inside surface, will be slid over matching sliding tracks 53a. Guiding tube 53 encompasses the optical fiber scanner and lens 136a. The guiding tube will be glued to a protective nylon sheath 55 that covers the entire endoscope; sheath 55 cannot be rotated. When the shuttle nut is rotated by the DC motor via the speedometer cable, the endoscope assembly will slide along the sliding track to perform focus tracking. The tracking resolution can be up to about 300 µm per rotation or about 0.85 µm per degree. The overall diameter of the endoscope including the protective sheath will be about 3.4 mm, which can easily interface with a standard endoscope through a 3.6-mm accessory port.

Other exemplary focus tracking mechanisms involve moving the focusing lens within the imaging compound lens assembly or the entire distal end of the endoscope assembly by: (1) direct mechanical translation; (2) hydraulic translation; or (3) electro-magnetic actuation. FIGS. 12A and 12B illustrate an OCT probe 150 in which a tubular field-actuated polymer 152 is used to move a lens longitudinally to vary the depth at which the focus point is located in a subject being scanned. The material from which tubular field-actuated polymer 152 is fabricated has the characteristic that in the presence of an applied voltage, it changes both in thickness and in length. Therefore, in exemplary OCT probe 150, a lead 156 is coupled to a terminal 154 on an outer surface of the tubular field-actuated polymer, while a terminal 158, which is disposed on the interior surface of the tubular field-actuated polymer, is coupled to ground. Also, the proximal end of tubular field-actuated polymer 152 is disposed against a stop 162, preventing it from moving within metal hypodermic tubing 78. The distal end of the tubular field-actuated polymer is connected to a support 164 that holds lens 124 and slides axially, thereby axially moving lens 124 to vary the focus of the optical system. When an appropriate voltage is applied to terminals 154 and 158, the tubular field-actuated polymer becomes thinner, but lengthens by an amount ΔL. This change in length causes support 164 to slide distally within the metal hypodermic tubing, shifting the location of the focal point of lens 124 from a point 166 to a point 166', by an amount equal to ΔL. The voltage level applied to terminals 154 and 158 can be selectively controlled to vary the position of the focal point of lens 124 by a desired amount. This same approach can alternatively be applied to any other lens within the optical system, to similarly vary the longitudinal position of the focal point, and thereby provide depth focus tracking.

FIG. 13 illustrates an OCT probe 190 in which a lens 194 and a lens 123 are both mounted within a transparent carrier 196, which slides longitudinally inside metal hypodermic tubing 78 in response to a fluid pressure, P, applied from a proximal pressure source (not shown) to a volume 200. Volume 200 is proximal the transparent carrier. A seal 198 around the periphery of transparent carrier 196 ensures that pressurized pneumatic fluid does not leak past the periphery of the transparent carrier. A helical spring 193 provides a restoring bias force that resists the distally directed force acting on the transparent carrier as a result of the pressure in volume 200. Of course, lens 194 and lens 123 can be replaced with a single lens. As transparent carrier 196 and the lenses are moved longitudinally in response to a change in the pressure within volume 200, focal point 202 also shifts longitudinally, enabling the depth focus tracking to be varied selectively as a function of the applied pressure. When the pressure is decreased, the spring causes transparent carrier 196 and the lenses to move toward their previous initial positions. It should be understood that the depth of focus can be changed using this scheme for focus tracking, without changing the focus size.

Finally, in FIG. 14, an exemplary OCT probe 210 includes a lens 218 and lens 124, both of which are fixed in place. A port 212 is formed in metal hypodermic tube 78, distal of lens 124. Port 212 is coupled through a flexible tube 214 to a vacuum pump or other suitable controlled vacuum source (not shown) that can vary the level of vacuum applied to a volume 216 that is distal of lens 124. The open end of metal hypodermic tube 78 is placed in sealing contact with tissue 220, and a desired level of vacuum (i.e., a fluid pressure lower than ambient) is applied. The reduced pressure within volume 216 draws tissue 220 into the open end of the device to an extent that can vary the depth at which light from lens 124 is focused within the tissue. Thus, by controlling the level of the negative gauge pressure or vacuum applied to volume 216, the depth focus tracking is readily controlled in accord with the present approach, to enable transverse scanning at successive different depths in the tissue. It will be understood that the image quality might be affected by the change in negative pressure applied to the tissue.

Experimental Demonstration

Experiments have been conducted to prove that the disclosed real-time simultaneous geometric focus and coherence gate tracking provide improvements as compared to conventional OCT imaging. An OCT system based on the OCT system of FIG. 7 was employed for the empirical testing. The modulator in the reference arm was employed to introduce sufficient Doppler frequency shift for achieving sensitive heterodyne OCT detection. In addition, a scanning grating-lens based optical delay line was used in the reference arm to compensate the dispersion caused by the phase modulator and to perform slow OPL scanning to track the coherence gate along with the beam focus in the sample arm.

Figure 1:
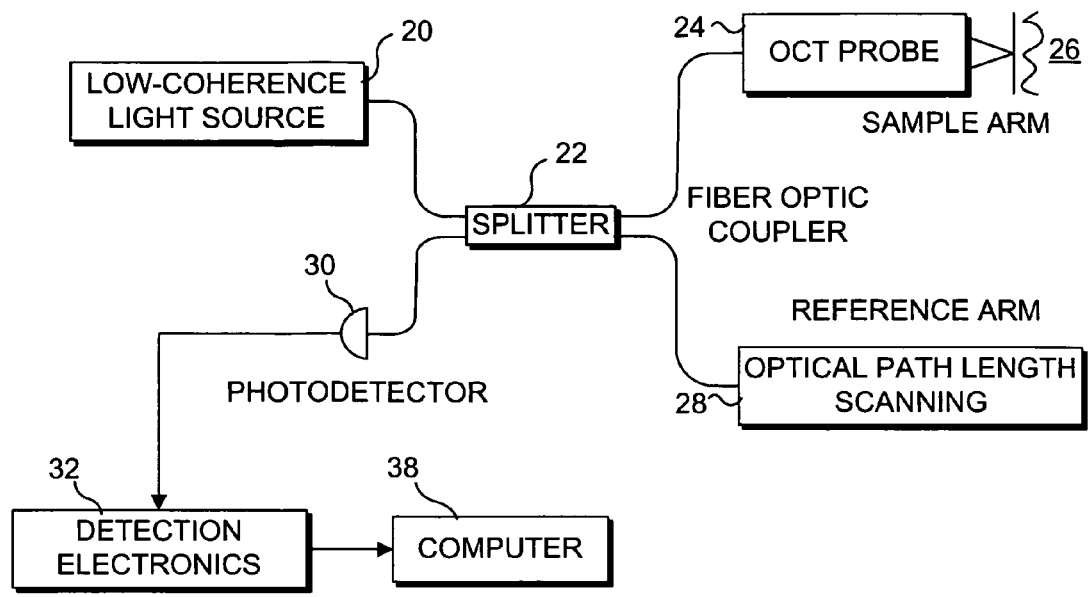
FIG. 1 (Prior Art) is a schematic block diagram of a typical OCT system.

FIGS. 15A-15C are OCT images of a tissue phantom (gelatin embedded with polystyrene spheres). FIG. 15A was acquired using a conventional OCT system (i.e., an OCT system consistent with that shown in FIG. 1) without focus tracking. FIG. 15B was acquired using the OCT system of FIG. 7, where the system was configured to implement geometric focus tracking but not coherence gate tracking (e.g., the reference arm OPL was set at the phantom surface and remained unchanged during beam focus tracking). FIG. 15C was acquired using the exemplary OCT system of FIG. 7, where the system was configured to simultaneously implement geometric focus tracking and coherence gate tracking (e.g., the reference arm OPL was varied during scanning to synchronize the OPL in the reference arm and the sample arm). The focus tracking was performed by mechanically translating the entire distal end of the endoscope assembly with a computer-controlled precision stage.

Note that in the OCT image of FIG. 15A, the size of spheres 306 appears larger outside the focal zone (indicated by dashed box 310) than the size of spheres 308 within the focal zone, which is an artifact caused by the large transverse spot size outside the focal zone. In the OCT image of FIG. 15B (which uses focus tracking but without simultaneous coherence gating tracking), the OCT measures the signal coming from a depth that is within the coherence gate but outside the beam focus. Thus, the transverse beam spot size was rather large, resulting in artifacts similar to those seen in FIG. 15A (i.e., some spheres 306 appear larger than some spheres 308, even though all spheres are identical in size). Referring now to the OCT image of FIG. 15C (in which both the beam focus and coherence gate were simultaneously tracked), note the improvement in image quality, with the spheres exhibiting minimal artifacts and signal degradation (i.e., most spheres appear to be the same size as sphere 308). This improved image quality results from the overlap of the coherence gate and the beam focus. All the images were acquired at a rate of 2 frames per second. FIGS. 16A, 16B, 17A, and 17B are also OCT images, and the conditions under which they were acquired are described in greater detail below.

With respect to FIGS. 16A and 16B, an empirical OCT system based on that shown in FIG. 7 employed a super luminescence diode with a center wavelength of 1.31 μm, and a FWHM bandwidth of 52 nm as a light source. The light was divided equally between the sample and reference arms. The reference arm included a phase-controlled optical delay line and an electro-optic phase modulator (EOM). The carrier frequency resulting from the phase delay line was set to zero. The EOM generated a carrier frequency of 7 MHz. The dispersion from the phase modulator crystal was compensated to the third order as described above, producing a measured, nearly optimal axial resolution of 15.6 μm in air.

The sample arm included a 2.4 mm diameter forward-viewing miniature probe (or endoscope), which utilized a single-mode fiber (SMF) cantilever resonated by a 4 quadrant PZT actuator to perform rapid lateral scanning, and a 0.25 pitch gradient index (GRIN) lens to focus the beam. In addition to a linear scanning pattern, the empirical single fiber OCT endoscope was configured to perform circular beam scanning, in which the two opposing pairs of PZT electrodes are driven by two synchronized sinusoidal waveforms with a 90° relative phase shift. The lateral scanning range (or the radius of scanning circle) was proportional to the drive voltage and the GRIN lens magnification. In the empirical studies, a rapid circular scanning at a 1.37 kHz repetition rate was utilized. The single fiber OCT probe exhibited a working distance of 2.7 mm, and a measured confocal parameter of 0.2 mm, which corresponds to a 12.9 μm transverse resolution. Different working distances and transverse resolutions are possible by choosing a GRIN lens with a different pitch number, and/or by changing the distance between the scanning fiber tip and the GRIN lens.

The rapid lateral scanning of the single fiber OCT endoscopic probe allowed the implementation of a lateral-priority scanning image acquisition sequence for real-time OCT imaging, e.g., fast transverse scanning followed by slow depth scanning, as schematically illustrated in FIG. 3 (i.e., lateral priority scanning). In conventional depth-priority OCT imaging, the depth scanning speed is approximately $Z_{depth}N_{xpixel}F$, where $Z_{depth}$ is the scanning depth, $N_{xpixel}$ is the number of transverse pixels, and F is the frame rate. In comparison, the depth scanning speed in lateral priority scanning is reduced to $Z_{depth}F$, and the depth scanning repetition rate is equivalent to the frame rate. The alleviated requirement on the depth scanning speed and repetition rate enables the beam focus to be shifted throughout the imaging depth by directly translating the single fiber OCT endoscopic probe. Preferably, the scanning fiber and optics are translated together. In general, the refractive indices of the medium above the sample and the sample itself are different, resulting in an OPL change in the sample arm during focus tracking. Referring to the simple model shown in FIG. 8, and Eqs (5), (6), and (7), note that Eq (7) can be used to determine the change in the OPL in the reference arm required for coherence gate tracking synchronized with the geometric focus tracking in the sample arm.

The above analysis (i.e., the discussion relating to FIG. 8, and Eqs (5), (6), and (7)), is for a sample with a uniform refractive index. In practice, an approximate average refractive index will be used when imaging biological tissue. Since the maximum OCT interference signal will only occur when the OPL in both arms are equal, the coherence gate must be tracked simultaneously with the geometric beam focus during focus tracking. Therefore, the OPL in the reference arm is scanned simultaneously to match the OPL in the sample arm as counted from the beam focus in the sample.

The small numerical aperture (NA=0.14) of the single fiber OCT endoscopic probe enables the OPL in the reference arm to be adjusted according to Eq (7) in real-time during focus tracking. Before imaging the sample, tilting mirror 122 in the delay line is set to its neutral position (referring to the optics in the reference arm) and the reference arm OPL is tuned to match the sample arm OPL. FIGS. 16A and 16B are OCT images acquired using the empirical OCT system described above, from a gelatin phantom embedded with 25 μm polystyrene spheres. FIG. 16A is an OCT image acquired without continuous focus tracking. FIG. 16B is an OCT image acquired with continuous focus tracking at a 1-Hz frame rate (other imaging parameters remained the same, except as noted below). In FIG. 16A, the focus was initially set at about 330 μm below the phantom surface and remained unchanged during the depth scan. The polystyrene microspheres within the focal zone, indicated by dashed lines, are clearly differentiated, while outside the focal zone, microspheres appear elongated in the transverse direction, as indicated in the enlarged sphere in box 310, due to the deterioration of the transverse resolution. FIG. 16A was collected by controlling the tilting mirror in the reference arm using a driving ramp waveform 73, as indicated in FIG. 16C.

The real-time OCT image collected using continuous focus tracking as shown in FIG. 16B was acquired from the same region of the sample as FIG. 16A, and was collected by actuating the tilting mirror in synchrony with the linear translation of the endoscope, using a drive waveform 75 of FIG. 16D to control the mirror in the reference arm. Essentially, the focus was initially set at $l_{sAir}$=0.1 mm above the sample surface. To perform focus tracking, the single fiber OCT endoscopic probe was translated over a distance $l_{sAir}$ towards the sample in air, while the reference arm path length remained unchanged (according to Eq. (7) where $\Delta OPL$=0, since $n_2$=1 when the focus travels in air). The endoscope was then further translated $l_{sSample}$=0.9 mm, corresponding to the focus tracking portion in the sample. A handheld, precision linear magnetic actuator was used to translate the endoscope. According to the above analysis, the beam focus moved a distance of $\delta_{Sample}$=$n_2 l_{sSample}$≈1.23 mm in the sample (e.g., in gelatin with $n_2$≈1.37). In order to simultaneously track the coherence gate with the geometric beam focus within the sample, the OPL in the reference arm was scanned over a total distance of $\Delta OPL$≈$(n_2^2-1)l_{sSample}$=0.79 mm, according to Eq. (7). The true imaging depth would be $\delta=l_{sAir}+\delta_{Sample}=1.33$ mm. As shown in FIG. 16B, the polystyrene microspheres are more clearly visualized, and retain their shape throughout the entire imaging depth, implying that the transverse resolution was approximately maintained within the entire imaging depth (i.e., compare the sphere in a box 312 from FIG. 16B with the sphere in a box 310 of FIG. 16A). The refractive index mismatch between the polystyrene microsphere and surrounding gelatin gives rise to multiple echoes or reflections. The echoes, shown in FIGS. 16A and 16B, are separated on the image by an OPL of $n_3D$, where $n_3$ is the refractive index of the microsphere ($n_3\sim1.6$) and D is the diameter of the image cross-section of the microsphere, with a maximum value of D~25 μm.

Note in FIG. 16A, the particles became elongated outside the focal zone due to the deterioration of the transverse resolution (box 310), while in the image of FIG. 16B, the imaged particle size was substantially constant throughout the entire imaging depth (box 312). The images were collected over 95% of the circular scan using a 1.31-μm SLD source and having a size of 1260×1160 pixels (~1.55×1.26 mm, transverse×depth). The incident power on the phantom was 2.85 mW.

To further illustrate the effects of focus tracking, the empirical OCT system and the variable focus single fiber OCT endoscopic probe was employed to image a freshly excised rabbit esophagus. The esophagus images were obtained after replacing the light source described above (with respect to the collection of images in FIGS. 16A and 16B) with an 825 nm light source having a 135 nm bandwidth, and replacing the EOM phase modulator with an acoustic-optic frequency modulator. The axial resolution was about 3 μm (in air) after dispersion compensation, and the transverse resolution was about 10.5 μm. The OCT image of FIG. 17A was acquired without focus tracking, while the image of FIG. 17B was acquired with synchronized focus tracking and coherence gate tracking, using the same imaging parameters as used to acquire the image of FIG. 17A. The epithelium, lamina propria, and muscularis mucosa are clearly delineated in both images, but are more prominent in the focus tracked image (i.e., the image of FIG. 17B). The blood vessels in the muscularis mucosa are also more evident in this focus tracked image. The images were collected over 95% of the circular scan using the above-noted 825 nm light source. The incident power on the sample was 9.3 mW. The image size is 820×730 pixels (~1.20×0.43 mm, transverse×depth).

Real-Time En Face Imaging

It should recognized that the dynamic focus tracking method presented here can easily be extended for en-face OCT imaging, which is possible when the modulator in the reference arm is used to introduce a Doppler frequency shift required for heterodyne detection. For en face OCT imaging, the required depth tracking speed is much lower than in the case of the OCT imaging discussed above (in regard to FIG. 3). At an imaging rate of 5 frames/s and assuming the thickness of each image slice is 10 μm, the focus tracking speed is about 50 μm/s. If available micromotors are not sufficiently stable at such low speeds, one solution is to rotate a driver shaft threaded into the shuttle nut through a speedometer cable using a galvanometer-driven reduction gear disposed at the proximal end of the endoscope, generally as shown in FIG. 11. With respect to en face OCT imaging, it will be understood that the imaging is layer-by-layer, and a 3-D image is built up slice-by-slice. To perform 2-D en face scanning that will produce a layer, both the X and Y quadrants of the PZT actuator are preferably driven by the triangle-modulated (or sinusoidally modulated) sinusoidal signals shown in FIG. 6B, with the X and Y waveforms 90° out of phase, creating spiral-scanning pattern 100, as shown in FIG. 6A. The scanning light beam spirals in and out to produce this pattern. However, other desired scanning patterns can be used in the alternative. The imaging frame rate is twice the triangular modulation frequency.

Form Factors for OCT Probes

While the concepts disclosed herein can be beneficially implemented in an OCT imaging system incorporating an endoscopic OCT sample probe, it should be recognized that the concepts described above can also be incorporated into OCT imaging systems including OCT sample probes with form factors configured for external imaging applications (i.e., OCT sample probes having larger form factors). Where the form factor of the OCT probe is not required to be small for use in internal applications (i.e., an endoscopic form factor), it should be recognized that many different mechanisms can be employed to implement the geometric focus tracking discussed above. The specific exemplary structures described in detail above have been selected because such structures generally illustrate approaches that enable a compact form factor to be achieved. Where space is not a premium, those of ordinary skill in the art will readily recognize that many additional alternatives can be implemented. In general, regardless of the specific structure that is is employed to facilitate geometric focus tracking, it is desirable for the focus tracking to be implemented without changing the optical beam profile. For example, deformable lenses can be used to selectively change the position of the focal point, however, the beam profile also changes as the lens deforms. In the context of the concepts disclosed herein, changing the beam profile is undesirable because a change in the beam profile is generally accompanied with a change in resolution. One aspect of the concepts disclosed herein involves an attempt to maintain the resolution of the imaging system during scanning to enhance the quality of the image. Implementing focus tracking using structures that would change the resolution during scanning is at odds with this goal. It should be recognized that the sample itself can change the beam profile, due to refractive effects, however, the imaging system is preferably configured to avoid inducing any beam profile changes on its own.

With respect to external use, the concepts described in detail above can be beneficially incorporated into an OCT imaging system configured for eye imaging and other applications. Such a system would not require an OCT sample probe having an endoscopic form factor.

Although the present development has been described in connection with the preferred form of practicing it and modifications thereto, those of ordinary skill in the art will understand that many other modifications can be made thereto within the scope of the claims that follow. Accordingly, it is not intended that the scope of protection for the novel concept in any way be limited by the above description, but instead be determined entirely by reference to the claims that follow.

The invention in which an exclusive right is claimed is defined by the following:

1. A method for achieving dynamic focus tracking in real-time optical coherence tomography (OCT), comprising the steps of:

(a) advancing an OCT probe to a position adjacent to a sample;

(b) actuating the OCT probe to initiate scanning of the sample using lateral priority scanning, said lateral priority scanning comprising moving a focal point of the OCT probe both transversely to achieve a transverse motion, and axially to achieve an axial motion, the transverse motion occurring generally along an axis that is substantially orthogonal to an axis of a light beam emitted by the OCT probe, and the axial motion occurring generally along an axis that is substantially parallel to the axis of the light beam emitted by the OCT probe, such that the transverse motion occurs relatively rapidly, and the axial motion occurs relatively slowly, the axial motion corresponding to geometric focus tracking, which changes an optical path length associated with the OCT probe during scanning; and (c) simultaneously performing coherence gate tracking during the scanning, such that an optical path length in a reference arm is synchronized with the optical path length associated with the OCT probe, thereby achieving dynamic focus tracking, the relatively slower axial motion enhancing a synchronization of the optical path length in the reference arm to the optical path length associated with the OCT probe.

2. The method of claim 1, wherein the OCT probe comprises an endoscopic-sized instrument, and the step of advancing the OCT probe to the position adjacent the sample comprises the step of introducing the OCT probe into a patient's body using endoscopic techniques.

3. The method of claim 1, wherein the step of performing geometric focus tracking during the scanning comprises the step of using a prime mover disposed within the OCT probe to move optical components of the OCT probe relative to the sample.

4. The method of claim 1, wherein the step of performing geometric focus tracking during the scanning comprises the step of using a prime mover disposed outside of the OCT probe to move optical components of the OCT probe relative to the sample.

5. The method of claim 1, wherein the step of performing geometric focus tracking during the scanning comprises the step of using a field-actuated polymer to move optical components of the OCT probe relative to the sample.

6. The method of claim 1, wherein the step of performing geometric focus tracking during the scanning comprises the step of using pressure to move optical components of the OCT probe relative to the sample.

7. The method of claim 6, wherein the step of using pressure to move optical components of the OCT probe relative to the sample comprises the step of using a positive pressure to move the optical components.

8. The method of claim 6, wherein the step of using pressure to move optical components of the OCT probe relative to the sample comprises the step of using a negative pressure to move the optical components.

9. The method of claim 1, wherein the step of simultaneously performing coherence gate tracking comprises the steps of:

(a) determining the change in the optical path length associated with the OCT probe focus tracking;

(b) determining a translation of optical components in the reference arm required to cause a corresponding change in the optical path length associated with the reference arm; and (c) translating optical components in the reference arm as required to synchronize the optical path length in the reference arm to substantially equal the optical path length associated with the OCT probe focus tracking.

10. The method of claim 9, further comprising the steps of repeating steps (a)-(c) to perform coherence gate tracking each time the optical path length associated with the OCT probe changes.

11. A method for improving image quality in real-time optical coherence tomography (OCT), comprising the steps of:

(a) advancing an OCT probe to a position adjacent to a sample;

(b) actuating the OCT probe to initiate lateral priority scanning of the sample, said lateral priority scanning comprising the step of moving a focal point of the OCT probe both transversely to achieve a transverse motion, and axially to achieve an axial motion, the transverse motion occurring generally along an axis that is substantially orthogonal to an axis of a light beam emitted by the OCT probe, and the axial motion occurring generally along an axis that is substantially parallel to the axis of the light beam emitted by the OCT probe, such that the transverse motion occurs relatively rapidly, and the axial motion occurs relatively slowly, the axial motion corresponding to geometric focus tracking, which changes an optical path length associated with the OCT probe during scanning, where moving the focal point of the OCT probe relative to the sample during the lateral priority scanning of the sample is implemented using at least one technique selected from the group consisting essentially of:

(i) using a positive pressure to move optical components of the OCT probe;

(ii) using a negative pressure to move optical components of the OCT probe;

(iii) using a field-actuated polymer to move optical components of the OCT probe;

(iv) using a prime mover disposed outside of the OCT probe to move optical components of the OCT probe; and (v) using a prime mover disposed within the OCT probe to move optical components of the OCT probe;

(c) determining a change in an optical path length associated with the OCT probe, the change in the optical path length resulting from the movement of the focal point;

(d) determining a translation of optical components in a reference arm required to cause a corresponding change in an optical path length associated with the reference arm; and (e) translating the optical components in the reference arm as required to synchronize the optical path length in the reference arm to substantially equal the optical path length associated with the OCT probe, thereby improving a quality of an image derived from the scanning of the sample, this relatively slower axial motion enhancing a synchronization of the optical path length in the reference arm to the optical path length associated with the OCT probe, thereby improving the focus tracking performance.

12. The method of claim 11, wherein the OCT probe comprises an endoscopic-sized instrument, and the step of advancing the OCT probe to the position adjacent the sample comprises the step of introducing the OCT probe into a patient's body using endoscopic techniques.

13. A system for achieving dynamic focus tracking in real-time optical coherence tomography (OCT), comprising:

(a) a low-coherence light source;
(b) a sample arm comprising an OCT probe configured to scan a sample, the sample arm exhibiting a first optical path length, the sample arm being optically coupled to the light source, the OCT probe being configured to move a focal point of the OCT probe relative to a sample during scanning of the sample, using at least one element selected from the group consisting essentially of:
  (i) a positive pressure source configured to move optical components of the OCT probe;
  (ii) a negative pressure source configured to move optical components of the OCT probe;
  (iii) a field-actuated polymer configured to move optical components of the OCT probe;
  (iv) a prime mover disposed outside of the OCT probe and configured to move optical components of the OCT probe; and
  (v) a prime mover disposed within the OCT probe and configured to move optical components of the OCT probe;
(c) a reference arm exhibiting a second optical path length, the reference arm being optically coupled to the light source;
(d) a detector optically coupled to the sample arm and the reference arm; and
(e) a processor and memory logically coupled to the detector, the sample arm and the reference arm, the processor being configured to execute a plurality of machine instructions residing in the memory to carry out the following functions:
  (i) actuating the OCT probe to initiate lateral priority scanning of the sample, said lateral priority scanning comprising moving a focal point of the OCT probe both transversely to achieve a transverse motion, and axially to achieve an axial motion, the transverse motion occurring generally along an axis that is substantially orthogonal to an axis of a light beam emitted by the OCT probe, and the axial motion occurring generally along an axis that is substantially parallel to the axis of the light beam emitted by the OCT probe, such that the transverse motion occurs relatively rapidly, and the axial motion occurs relatively slowly, the axial motion corresponding to geometric focus tracking, which changes an optical path length associated with the OCT probe during scanning;
  (ii) controlling the OCT probe to implement geometric focus tracking during the scanning, thereby changing the first optical path length using at least one of the techniques identified above; and
  (iii) simultaneously performing coherence gate tracking, such that the second optical path length is synchronized with the first optical path length during scanning, thereby achieving dynamic focus tracking, the relatively slower axial motion enhancing a synchronization of the second optical path length in the reference arm to first optical path length associated with the OCT probe, thereby improving the focus tracking performance.

14. The system of claim 13, wherein the plurality of machine instructions, when executed by the processor, further carry out the following functions:
  (a) calculating a change in the first optical path length due to the geometric focus tracking;
  (b) calculating a translation of optical components in the reference arm required to cause a corresponding change in the second optical path length; and
  (c) translating the optical components in the reference arm as required to synchronize the first optical path length with the second optical path length during scanning.

15. The system of claim 13, wherein the plurality of machine instructions, when executed by the processor, further carry out the function of controlling the OCT probe to implement lateral priority scanning.

16. The system of claim 13, wherein the OCT probe is configured to implement the geometric focus tracking without changing a Gaussian beam profile associated with the OCT probe.

17. The system of claim 13, wherein the OCT probe comprises an endoscopic instrument.

18. The system of claim 13, wherein the reference arm further comprises a translation stage configured to translate optical components in the reference arm to enable the second optical path length to be synchronized with the first optical path length.

19. The system of claim 13, further comprising:
  (a) a modulator configured to introduce at least one of a sufficient Doppler frequency and a sufficient phase shift for performing optical heterodyne detection; and
  (b) a mechanism to compensate for the dispersion of the modulator, optical components of the system, and the sample to be imaged, to facilitate optimal OCT axial resolution.

20. The system of claim 19, wherein the modulator is part of the reference arm.

* * * * *

UNITED STATES PATENT AND TRADEMARK OFFICE
CERTIFICATE OF CORRECTION

PATENT NO. : 7,349,098 B2
APPLICATION NO. : 11/332780
DATED : March 25, 2008
INVENTOR(S) : Xingde Li Page 1 of 1

It is certified that error appears in the above-identified patent and that said Letters Patent is hereby corrected as shown below:

| | |
|---|---|
| Column 1, line 21 | The paragraph entitled "Government Rights" should be replaced with the following --This invention was made with U.S. Government support under grant No. 1 R21 CA96633-D awarded by the National Institutes of Health, and under grant No. BES-0348720 awarded by the National Science Foundation. The U.S. Government has certain rights in the invention.-- |
| Column 5, line 18 | after "and" insert --in-- |
| Column 12, line 60 | delete "dept" and insert therefor --depth-- |
| Column 17, line 50 | after "should" insert --be-- |

Signed and Sealed this

Nineteenth Day of August, 2008

JON W. DUDAS
*Director of the United States Patent and Trademark Office*

UNITED STATES PATENT AND TRADEMARK OFFICE
CERTIFICATE OF CORRECTION

PATENT NO. : 7,349,098 B2
APPLICATION NO. : 11/332780
DATED : March 25, 2008
INVENTOR(S) : Xingde Li Page 1 of 1

It is certified that error appears in the above-identified patent and that said Letters Patent is hereby corrected as shown below:

Column 1, line 21    The paragraph entitled "Government Rights" should be replaced with the following: --This invention was made with U.S. Government support under grant Nos. 1 R21 CA96633-D and CA094303 awarded by the National Institutes of Health, and under grant No. BES-0348720 awarded by the National Science Foundation. The U.S. Government has certain rights in the invention.--

Signed and Sealed this

Ninth Day of December, 2008

JON W. DUDAS
*Director of the United States Patent and Trademark Office*